United States Patent
Kramer et al.

(12)

(10) Patent No.: US 6,401,244 B1
(45) Date of Patent: Jun. 11, 2002

(54) WELDING HELMET AND FACE PLATE

(75) Inventors: Rafael Kramer, Glenview, IL (US); James David Termeer, Ahtrim, NH (US)

(73) Assignee: Sellstrom Manufacturing Co., Palatine, IL (US)

( * ) Notice: Subject to any disclaimer, the term of this patent is extended or adjusted under 35 U.S.C. 154(b) by 0 days.

(21) Appl. No.: 09/805,793

(22) Filed: Mar. 13, 2001

(51) Int. Cl.$^7$ ................................................ A61F 9/00
(52) U.S. Cl. .............................................................. 2/8
(58) Field of Search ................................ 2/7, 8, 9, 424, 2/429; 219/147

(56) References Cited

U.S. PATENT DOCUMENTS

| | | | |
|---|---|---|---|
| 1,919,927 A | * | 7/1933 | Bowers |
| 2,152,865 A | * | 4/1939 | Bowers |
| 2,270,028 A | | 1/1942 | Anderson |
| 2,628,530 A | | 2/1953 | Rabben |
| 3,251,065 A | | 5/1966 | Caldwell |
| 3,257,667 A | | 6/1966 | Anderson |
| 3,415,595 A | | 12/1968 | Nelson |
| 3,440,661 A | | 4/1969 | Newcomb |
| 3,444,561 A | | 5/1969 | Boyer |
| 3,458,865 A | * | 8/1969 | Simpson et al. |
| 3,577,563 A | | 5/1971 | Raschke |
| 3,599,239 A | | 8/1971 | Tatum |
| 3,866,244 A | | 2/1975 | Ruck |
| 4,101,979 A | | 7/1978 | Tarrone |
| 4,114,198 A | | 9/1978 | Sands |
| 4,293,757 A | | 10/1981 | Niemi |
| 4,422,185 A | | 12/1983 | Cook |
| 4,525,876 A | | 7/1985 | Bailey |
| 4,646,363 A | | 3/1987 | Wood |
| 4,679,255 A | | 7/1987 | Kuhlman |
| 4,686,711 A | | 8/1987 | Budmiger |
| 4,694,141 A | | 9/1987 | Hahn |
| 4,774,723 A | | 10/1988 | Ruck |
| 4,853,973 A | | 8/1989 | Boochard |
| 4,884,302 A | * | 12/1989 | Foehl |
| D308,266 S | | 5/1990 | Van Wyk |
| 4,937,879 A | | 7/1990 | Hall et al. |
| D310,276 S | | 8/1990 | Fuerthbauer et al. |
| 4,945,572 A | | 8/1990 | Rosen |
| D310,432 S | | 9/1990 | Boochard |
| 4,989,598 A | | 2/1991 | Berg et al. |
| 5,012,528 A | | 5/1991 | Pernicka et al. |
| 5,062,156 A | | 11/1991 | Siegal |
| D322,493 S | | 12/1991 | Metzger |
| D324,588 S | | 3/1992 | Metzger |
| 5,123,114 A | | 6/1992 | Desanti |
| 5,140,707 A | | 8/1992 | Johnson |
| 5,170,501 A | | 12/1992 | White |
| 5,189,735 A | | 3/1993 | Grona |
| 5,191,468 A | | 3/1993 | Mases |

(List continued on next page.)

FOREIGN PATENT DOCUMENTS

| | | |
|---|---|---|
| AU | 7616617 | 2/1978 |
| GB | 2225646 | 6/1990 |
| WO | 88/06030 | 8/1988 |

*Primary Examiner*—Rodney M. Lindsey
(74) *Attorney, Agent, or Firm*—Mayer, Brown, Rowe & Maw

(57) ABSTRACT

A welding helmet comprising: a face portion defined by a wall about the perimeter of the face portion, extending toward the interior of the welding helmet; a flange extending from the interior end of the wall; a sloped outer portion about the exterior perimeter of the face portion; and at least one opening in the flange adjacent a first portion of the wall, the at least one opening having a protrusion therein protruding parallel to the flange. The welding helmet may also comprise a plurality of channels in a second portion of the wall. The welding helmet may also include a face plate for covering the face portion of the welding helmet comprising a bezel and an interior groove about the perimeter of the bezel.

26 Claims, 6 Drawing Sheets

U.S. PATENT DOCUMENTS

| | | |
|---|---|---|
| 5,224,219 A | 7/1993 | Edwards et al. |
| 5,319,808 A | 6/1994 | Bishop et al. |
| 5,337,419 A | 8/1994 | Russell |
| D353,691 S | 12/1994 | Scanlon |
| D355,053 S | 1/1995 | Honrud |
| D365,666 S | 12/1995 | Gumpp |
| D366,540 S | 1/1996 | Elias |
| 5,533,206 A | 7/1996 | Petrie et al. |
| 5,548,448 A | 8/1996 | Wagner |
| 5,561,855 A | 10/1996 | McFall |
| 5,619,754 A | 4/1997 | Thurwanger et al. |
| 5,669,070 A | 9/1997 | Bennett et al. |
| D393,933 S | 4/1998 | Huh |
| D394,732 S | 5/1998 | Huh |
| 5,749,096 A | 5/1998 | Fergason et al. |
| D398,421 S | 9/1998 | Crafoord et al. |
| 5,806,101 A | 9/1998 | Thurwanger et al. |
| 5,813,049 A | 9/1998 | Xu |
| 5,857,215 A | 1/1999 | Fergason et al. |
| 5,896,579 A | 4/1999 | Johnson et al. |
| 5,959,705 A | 9/1999 | Fergason |
| D419,727 S | 1/2000 | Verkic et al. |
| 6,021,520 A | 2/2000 | Wang-Lee |
| D431,328 S | 9/2000 | Tanner |
| 6,185,739 B1 | 2/2001 | Verkic et al. |

\* cited by examiner

WELDING HELMET AND FACE PLATE

BACKGROUND OF THE INVENTION

1. Field of the Invention

The present invention relates generally to a welding helmet. Particularly, the present invention is directed to a welding helmet and a face plate for a welding helmet.

2. Description of Related Art

Welding helmets are commonly used in the art as an aid to protecting the wearer from dangers such as sparks, heat, or flashes of light, specifically ultraviolet and infrared light. Typical welding helmets cover the front and/or sides of the head and include a relatively transparent front portion to see through. It is well known that the intense brightness and heat associated with welding activity can damage the eye, including possibly causing blindness. The transparent portion, therefore, may be a specially designed glass or plastic material to protect the user's eyes from intense heat and light generated by the welding activity. The transparent portion operates by filtering out harmful light and/or dimming visible light and harmful portions of the ultraviolet and infrared spectra.

Many welding helmets consist of a helmet body and a separate face plate that snaps into the front of the helmet. Although popular, many of these helmets suffer from the disadvantage of not creating an adequate seal between the face plate and the helmet. Consequently, light may seep through the helmet at the perimeter of the face plate where it is connected to the helmet. This is especially dangerous if there is a sudden burst of intense light. Under that circumstance, the welding helmet may not sufficiently protect the user's eyes from damaging, and possibly blinding, light.

There thus remains a need for an efficient and economic welding helmet that reduces seepage of light into the helmet.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

A feature of an embodiment of the present invention is a welding helmet comprising a face portion defined by a wall about the perimeter of the face portion, extending toward the interior of the welding helmet. Yet another feature of an embodiment of the present invention is a flange extending from the interior end of the wall towards the center of the face portion. A further feature of an embodiment of the present invention is a sloped outer portion about the exterior perimeter of the face portion. Another feature of an embodiment of the present invention is a pair of openings in the flange adjacent the top portion of the wall, the openings each having a protrusion therein protruding parallel to the flange. Yet a further feature of an embodiment of the present invention is a plurality of channels in the bottom portion of the wall. An advantage of the present invention is that a face portion is created that can be completely covered by a face plate to reduce seepage of harmful light.

Yet another feature in an embodiment of the present invention is a face plate for covering a face portion of a welding helmet comprising a bezel including a plurality of barbs extending therefrom. Another feature of an embodiment of the face plate according to the present invention is a pair of tabs having holes therein, extending from the interior side of the bezel. Another feature of an embodiment according to the present invention is an interior groove about the perimeter of the bezel. An advantage of an embodiment of the present invention is that connections between the face plate and the helmet are in the interior of the helmet to reduce seepage of harmful light.

It is to be understood that both the foregoing general description and the following detailed description are exemplary and are intended to provide further explanation of the invention claimed.

The accompanying drawings, which are incorporated in and constitutes part of this specification, are included to illustrate and provide a further understanding of the method and system of the invention. Together with the description, the drawings serve to explain the principles of the invention.

DETAILED DESCRIPTION OF THE PREFERRED EMBODIMENT

Reference will now be made in detail to the present preferred embodiments of the invention, an example of which is illustrated in the accompanying drawings. The present embodiments of the invention will be described in conjunction with the detailed description that follows.

For purpose of explanation and illustration, and not limitation, an exemplary embodiment of the system in accordance with the invention is shown in FIGS. 1–6.

Figure 1:
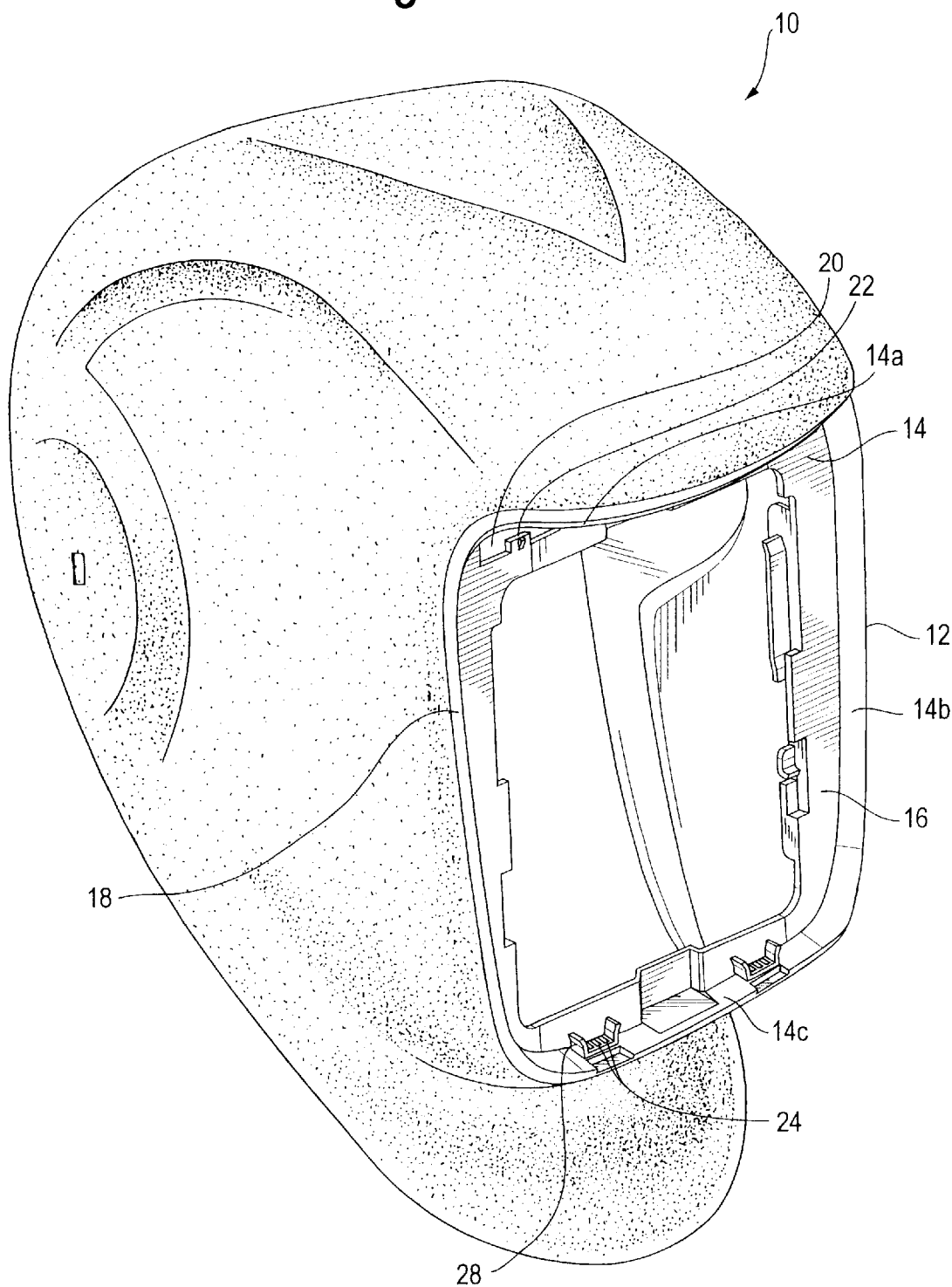
FIG. 1 is an elevated perspective view of an embodiment of a welding helmet in accordance with the invention.
Figure 2:
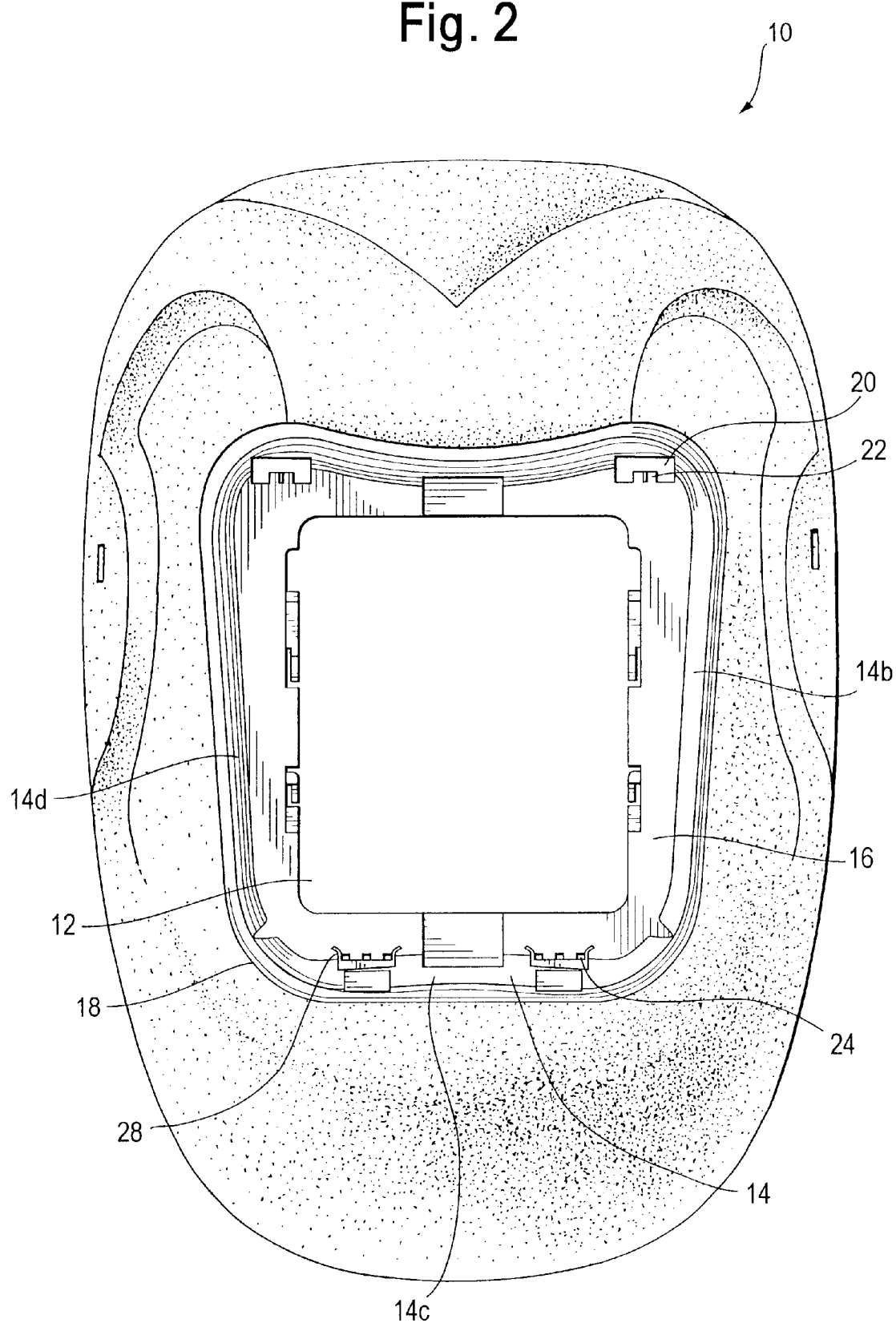
FIG. 2 is a front elevated view of view of an embodiment of a welding helmet in accordance with the invention.
Figure 3:
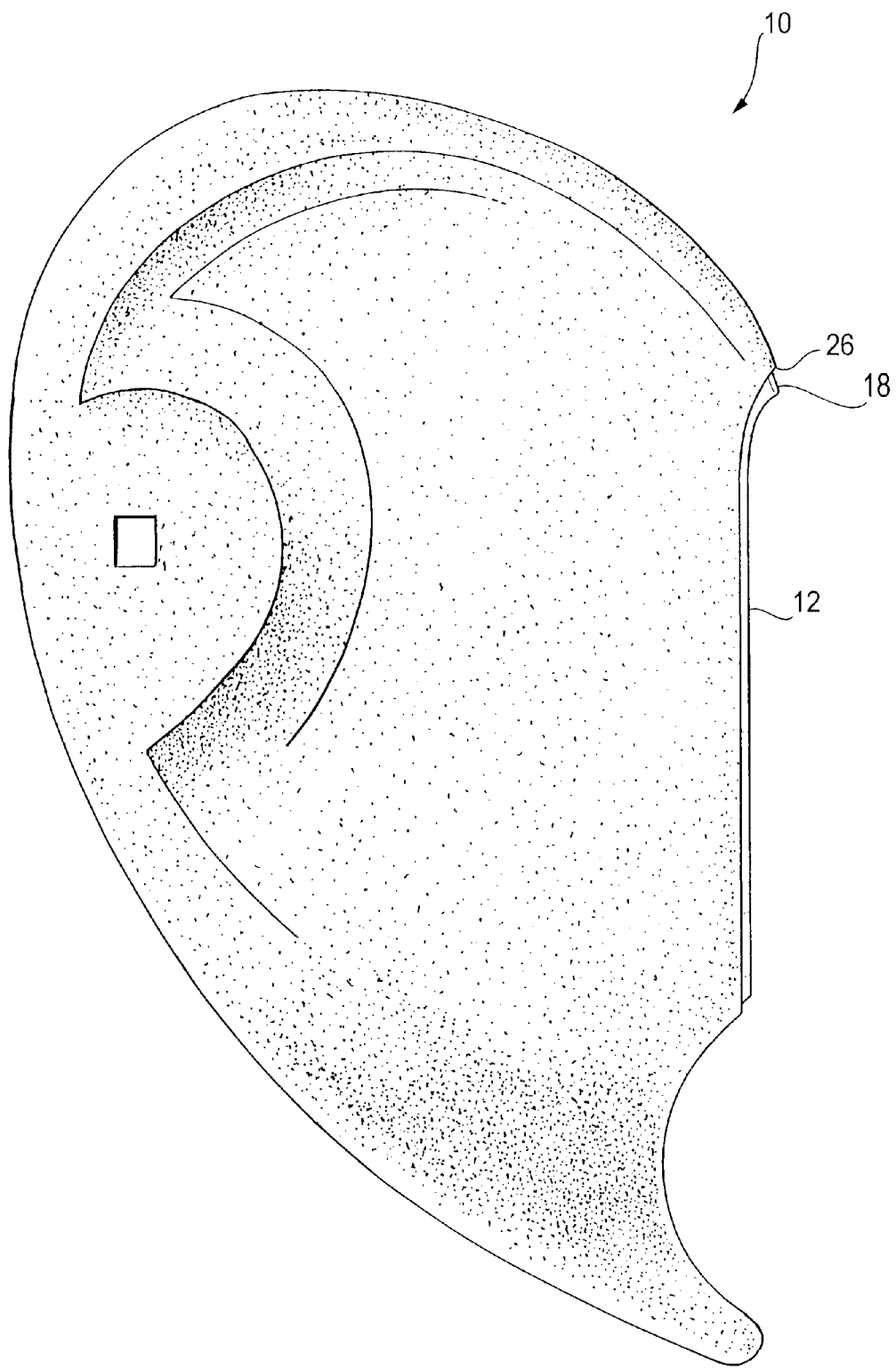
FIG. 3 is an elevated side view of an embodiment of a welding helmet in accordance with the invention.

As shown in FIGS. 1–3, an embodiment of the invention includes a welding helmet 10. In the preferred embodiment, the helmet 10 is made of plastic or a high density polyester material, although other suitable materials may be known in the art. Although the embodiments shown with respect to the present invention include various designs and ornamentation, it should be apparent to one skilled in the art, and it is intended that the present invention can be practiced with any type, shape or design of welding helmet. For example, the present invention may be embodied in the welding helmet 10 having a large side and neck portions, or in welding helmets largely comprising only a front portion with minimal or no side, top or neck portions. In addition, it should be apparent that the ornamentation for the welding helmet 10 is purely a design choice and is not germane to the present invention.

The welding helmet 10 of the present embodiment has a solid structure comprising an interior and exterior, and comprises a face portion, designated generally at 12 opening into the interior of the helmet 10. In operation, the face portion 12 is located at the front of helmet 10 and generally allows for the placement of a transparent shield to allow viewing. In many welding helmets, the transparent shield is made of a treated glass or plastic, such as a polarized pane of glass or plastic, to filter brightness and minimize the user's exposure to intense light as a result of the welding activity. In addition, it is well known in the art to provide electronic shielding lenses which automatically darken in the presence of light. The face portion 12 of the present embodiment is enlarged for maximum viewing comfort. However, the present invention is not so limited, and the face portion 12 can be sized according to any design preference sufficient to allow viewing.

As most clearly seen in FIG. 3, the helmet 10 further comprises a sloped outer portion 18 about the entire exterior perimeter of the face portion 12. In the present embodiment, the sloped outer portion 18 comprises a thin surface extending all along its length in a plane parallel to, but slightly offset from, the surface of the welding helmet 10 at the contour of the face portion 12. The sloped outer portion 18 offset from the welding helmet 10 at the contour of the face portion 12 creates a trough 26. In other embodiments of the present invention, the sloped outer portion 18 may protrude along some other plane, or may be of a variable width about its length.

The face portion 12 of the present embodiment is defined by a wall 14 which extends from the distal end of the sloped outer portion 18 towards the interior of the helmet 10. The wall 14 comprises top 14a, two side 14b, 14d, and bottom 14c portions.

A flange 16 extends from the interior end of the wall 14. In the preferred embodiment, the flange 16 extends perpendicularly to the wall 14. However, the present invention is not so limited, and the flange 16 may extend at other angles relative to the wall 14 without departing from the scope of the invention. In addition, the flange 16 may be of any suitable width to allow the presence of any securing means thereon, such as the openings 20 described below.

The bottom portion 14c of the wall 14 contains a plurality of channels 24. In the present embodiment, the helmet 10 is provided with two sets of three channels 24. In the preferred embodiment, blinders 28 are provided along side each set of channels 24 to prevent light from seeping in from the sides. However, the present invention may be practiced according to innumerable embodiments with respect to the channels, including without limitation, any number of sets of channels (including a single set) such that the bottom portion 14c contains a plurality of channels. Moreover, the present invention is not limited to embodiments having channels along the bottom portion 14c. For example, the channels 24 may be placed anywhere along the wall 16.

The flange 16 according to the present embodiment comprises a pair of openings 20 adjacent the top portion 14a of the wall 14. Each opening 20 has a protrusion 22 therein which protrudes at least partially into the opening 20 parallel to the flange 16. Although the present embodiment is practice with a pair of openings 20, other embodiments may include a single opening, or more openings, depending upon the design choice and the amount of openings sufficient to secure a face plate to the helmet 10. In addition, alternative embodiments of the present invention may include openings 20 along other portions of the flange 16 apart from the position adjacent the top portion 14a of the wall 14. In the preferred embodiment, the openings 20 are placed opposite the channels 24. However, the present invention is not intended to be so limited. For example, alternative embodiments may include sets of tabs without barbs and channels. Alternatively, embodiments may include barbs without tabs.

Figure 4:
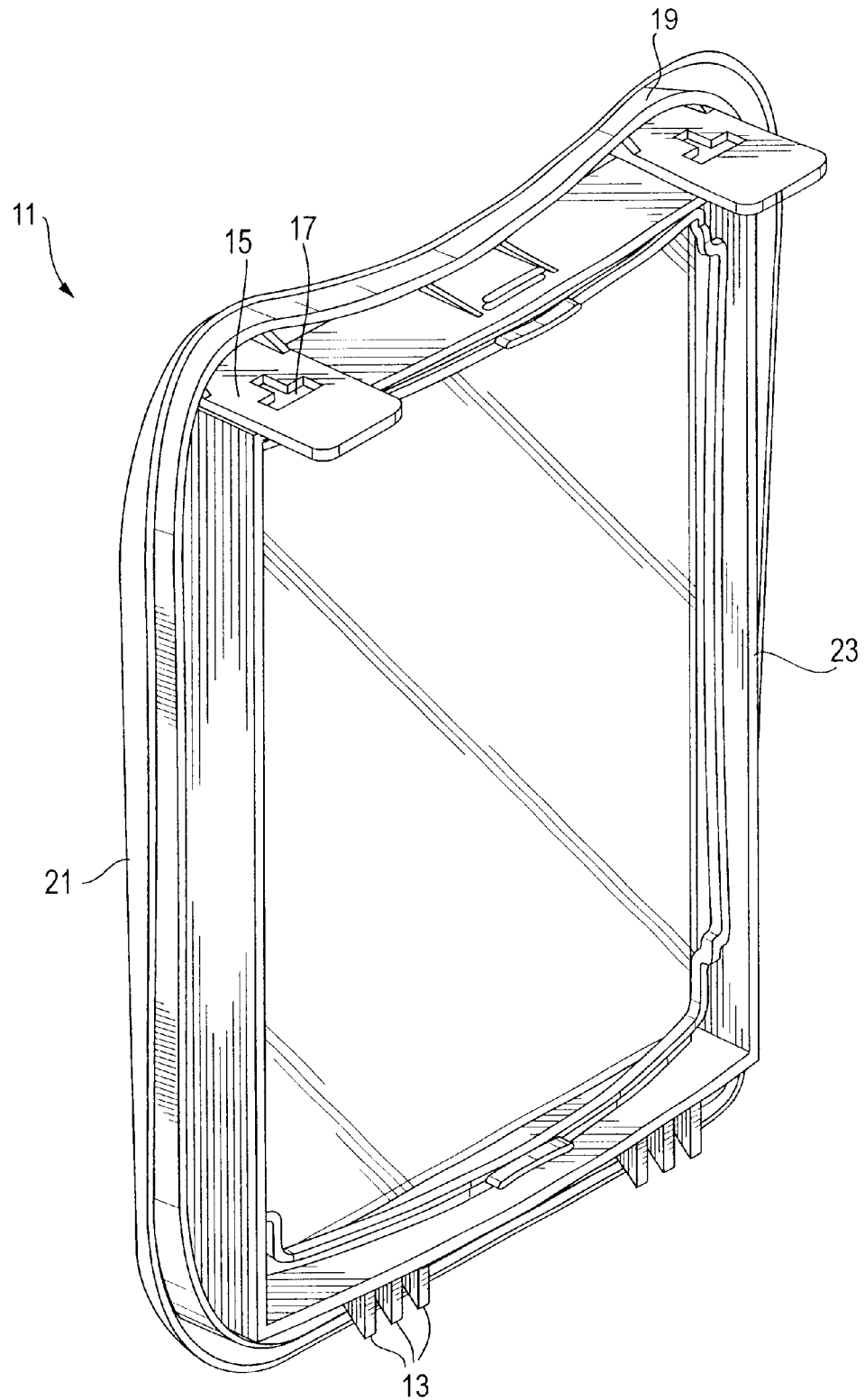
FIG. 4 is an elevated perspective view of an embodiment of a face plate in accordance with the invention.
Figure 5:
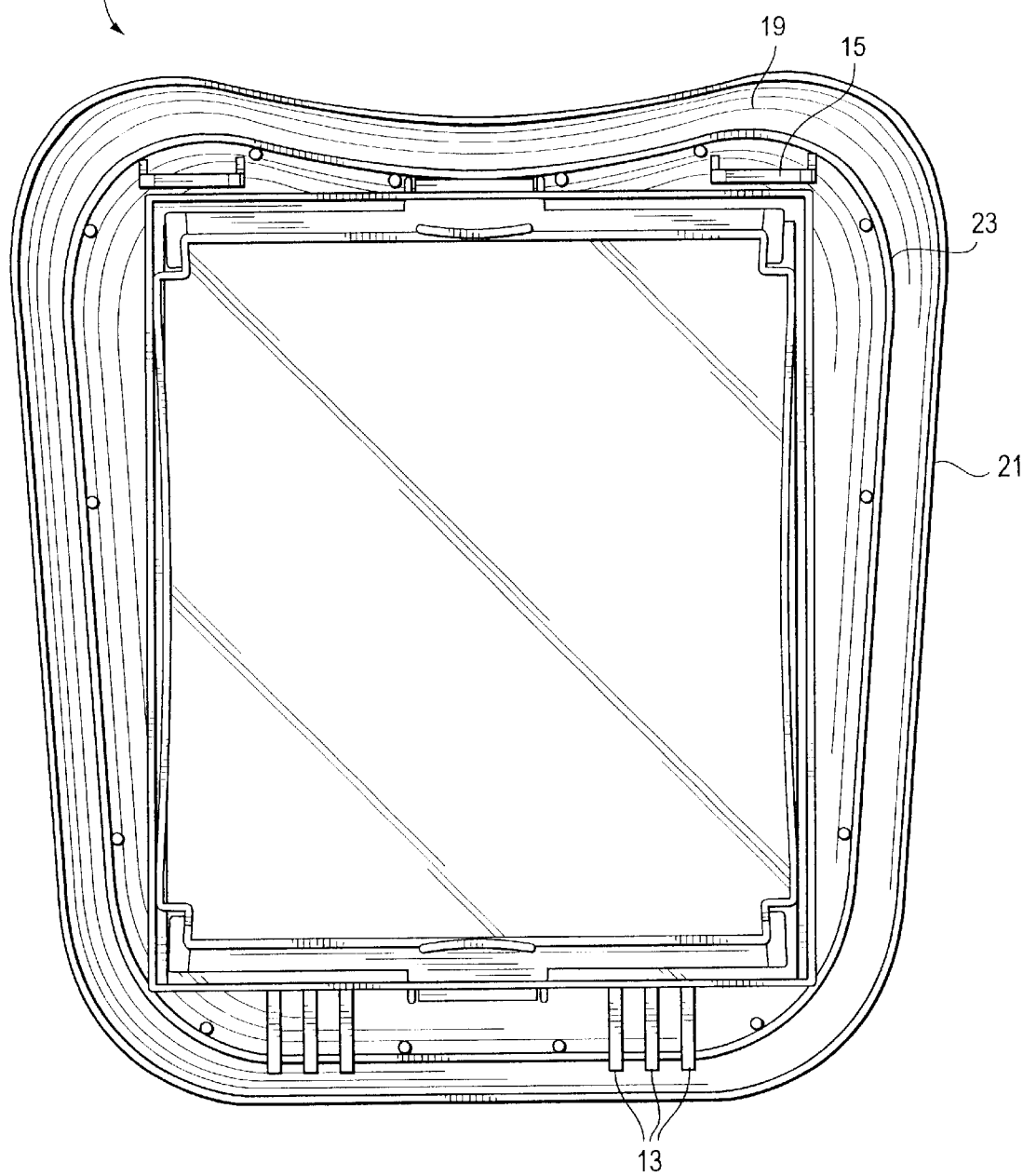
FIG. 5 is a rear elevated view of an embodiment of a face plate in accordance with the invention.
Figure 6:
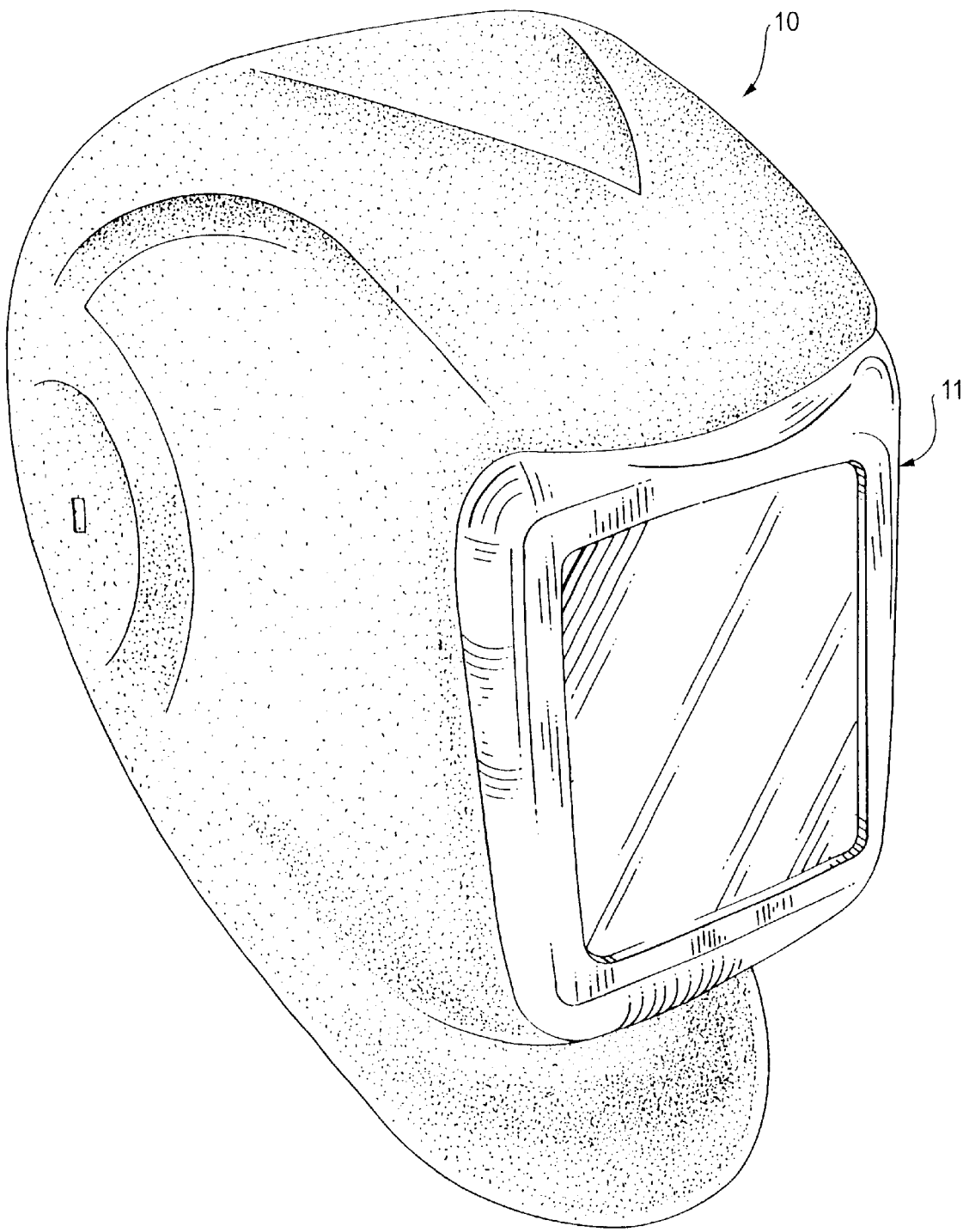
FIG. 6 is an elevated perspective view of an embodiment of the present invention.

Another aspect of the present invention includes a face plate, such as the face plate 11 embodied in FIGS. 4 and 5. The face plate 11 according to the present embodiment comprises a bezel 21 having a generally curved and sloped contour. As best seen in FIG. 6, the face plate 11 is adapted to fit over the face portion 12, to overlap and cover the sloped outer portion 18 of the face portion. The face plate 11 includes a plurality of barbs 13 adapted to fit into the channels 24.

The insertion of the barbs 13 into the channels 24 provides one means for securing the face plate 11 to the face portion 12 of the welding helmet. In addition, the positioning of the barbs 13 completely behind the bezel 21 and the placement of the channels 24 along the wall 14 towards the interior of the helmet 10 ensures that gaps created at the point of connection of the face plate 11 to the helmet 10 are shielded by the bezel 21. Thus, the present embodiment of the welding helmet according to the present invention minimizes leakage of intense, harmful light into the interior of the welding helmet 10 where such intense light could potentially do damage to a user's eyes and skin.

The face plate 11 further comprises a pair of tabs 15 having holes thereon 17, extending from the interior of the bezel 21. The tabs 15 are adapted to fit into the openings 20, and the protrusions 22 snap into the holes 17 to lock the face plate 11 to the welding helmet 10, and thus provide yet another means for securing the face plate 11 to the welding helmet 10. In the preferred embodiment, the tabs 15 and protrusions 22 are made of a resilient material such that the tabs can be bent upwards to disengage the protrusions 22 from the holes 17 and remove the face plate 11 from the helmet 10.

The face plate 11 of the present embodiment further comprises an interior groove 19 about the perimeter of the bezel 21. In the present embodiment, the groove 19 is formed with a rib 23 along the interior of the bezel 21. Preferably, the rib 23 is a continuous and uninterrupted about the interior of the bezel 21. As the face plate 11 is placed over the face portion 12 of the helmet 10, the groove 19 receives the sloped outer portion 18 of the face portion 12. The distal end of the bezel 21 abuts the trough 26 created by the offset of the sloped outer portion 18 from the helmet 10. Thus, all of the connections between the face plate 11 and helmet 10 are obscured by the bezel 21. Moreover, the sloped outer portion 18 functions as a flange behind the abutting edges of the bezel 21 and trough 26 to further minimize leakage of harmful light through or around the face portion 11.

It will be apparent to those skilled in the art that various modifications and variations can be made in the disclosed embodiments of the present invention without departing from the spirit or scope of the invention. Thus, it is intended that the present invention include modifications and variations that are within the scope of the appended claims and their equivalents.

What is claimed is:

1. A welding helmet having an interior, the welding helmet comprising:

a face portion defined by a wall about a perimeter of the face portion, extending from an exterior end at an exterior perimeter of the face portion to an interior end toward the interior of the welding helmet, and having top, bottom and side portions;

a flange extending from the interior end of the wall;

a sloped outer portion about the exterior perimeter of the face portion;

at least one opening in the flange adjacent a first portion of the wall, said at least one opening having a protrusion therein protruding parallel to the flange;

a plurality of channels in a second portion of the wall;

a face plate for covering the face portion comprising a bezel comprising:

a plurality of barbs adapted to fit in the channels;

at least one tab having a hole therein, extending from an interior side of the bezel adapted to fit into the at least one opening in the flange and receive the protrusion; and an interior groove about a perimeter of the bezel adapted to receive the sloped outer portion.

2. The welding helmet of claim 1 wherein the face plate further comprises a transparent member.

3. The welding helmet of claim 1 comprising a pair of openings.

4. The welding helmet of claim 1 comprising a pair of tabs.

5. The welding helmet of claim 1 wherein the at least one opening is adjacent the top portion of the wall.

6. The welding helmet of claim 1 wherein the plurality of channels are in the bottom portion of the wall.

7. A welding helmet having an interior, the welding helmet comprising:
   a face portion defined by a wall about a perimeter of the face portion, extending from an exterior end at an exterior perimeter of the face portion to an interior end toward the interior of the welding helmet, and having top, bottom and side portions;
   a flange extending from the interior end of the wall;
   a sloped outer portion about the exterior perimeter of the face portion;
   a face plate for covering the face portion comprising a bezel comprising:
      a plurality of barbs;
      at least one tab having a hole therein, extending from an interior side of the bezel; and
      an interior groove about a perimeter of the bezel adapted to receive the sloped outer portion;
   at least one means for securing the face plate to the welding helmet, wherein the securing means is covered by the bezel.

8. The welding helmet of claim 7 wherein the face plate further comprises a transparent member.

9. The welding helmet of claim 7 wherein the at least one means for securing the face plate to the welding helmet comprises at least one opening in the flange adjacent a first portion of the wall, said at least one opening having a protrusion therein protruding parallel to the flange, and at least one tab having a hole therein, extending from the interior side of the bezel adapted to fit into the at least one opening in the flange and receive the protrusion.

10. The welding helmet of claim 9 comprising a pair of tabs.

11. The welding helmet of claim 9 comprising a pair of openings.

12. The welding helmet of claim 9 wherein the at least one means for securing the face plate to the welding helmet comprises a plurality of channels in a portion of the wall, and wherein the plurality of barbs are adapted to fit in the channels.

13. A welding helmet having an interior, the welding helmet comprising:
   a face portion defined by a wall about a perimeter of the face portion, extending from an exterior end at an exterior perimeter of the face portion to an interior end toward the interior of the welding helmet, and having top, bottom and side portions;
   a flange extending from the interior end of the wall;
   a sloped outer portion about the exterior perimeter of the face portion;
   a face plate for covering the face portion comprising a bezel comprising:
      a plurality of barbs;
      at least one tab having a hole therein, extending from an interior side of the bezel; and
      an interior groove about a perimeter of the bezel adapted to receive the sloped outer portion;
   a first means for securing the face plate to the welding helmet; and
   a second means for securing the face plate to the welding helmet;
   wherein the first and second securing means are obstructed by the bezel.

14. The welding helmet of claim 13 wherein the face plate further comprises a transparent member.

15. The welding helmet of claim 13 wherein the first means for securing the face plate to the welding helmet comprises at least one opening in the flange adjacent a first portion of the wall, said at least one opening having a protrusion therein protruding parallel to the flange, and at least one tab having a hole therein, extending from the interior side of the bezel adapted to fit into the at least one opening in the flange and receive the protrusion.

16. The welding helmet of claim 15 comprising a pair of tabs.

17. The welding helmet of claim 15 comprising a pair of openings.

18. The welding helmet of claim 13 wherein both the first and second means for securing the face plate to the welding helmet comprise at least one opening in the flange adjacent a first portion of the wall, said at least one opening having a protrusion therein protruding parallel to the flange, and at least two tabs having holes therein, extending from the interior side of the bezel adapted to fit into each of the at least one openings in the flange and receive the protrusion.

19. The welding helmet of claim 13 wherein the second means for securing the face plate to the welding helmet comprises a plurality of channels in a portion of the wall, and wherein the plurality of barbs are adapted to fit in the channels.

20. The welding helmet of claim 13 wherein both the first and second means for securing the face plate to the welding helmet comprise a plurality of channels in a portion of the wall, and wherein the plurality of barbs are adapted to fit in the channels.

21. The welding helmet of claim 13 wherein the first securing means and the second securing means are located on opposite portions of the face portion.

22. A welding helmet having an interior, the welding helmet comprising:
   a face portion defined by a wall about a perimeter of the face portion, extending toward the interior of the welding helmet;
   a flange extending from an interior end of the wall;
   a sloped outer portion about an exterior perimeter of the face portion;
   at least one opening in the flange adjacent a first portion of the wall, said at least one opening having a protrusion therein protruding parallel to the flange;
   a plurality of channels in a second portion of the wall.

23. The welding helmet of claim 22 comprising a pair of openings.

24. The welding helmet of claim 22 wherein the at least one opening is adjacent a top portion of the wall.

25. The welding helmet of claim 22 wherein the plurality of channels are in a bottom portion of the wall.

26. A face plate for covering a face portion of a welding helmet comprising:
   a bezel comprising a plurality of barbs extending therefrom; a pair of tabs having holes therein, extending from an interior side of the bezel; and an interior groove about a perimeter of the bezel.

* * * * *